US008546086B2

(12) United States Patent
Schrattenholz

(10) Patent No.: US 8,546,086 B2
(45) Date of Patent: Oct. 1, 2013

(54) USE OF NEUREGULIN-β AS AN INDICATOR AND/OR TARGET

(75) Inventor: Andre Schrattenholz, Mainz (DE)

(73) Assignee: Mind-NRG SA, Geneva (CH)

( * ) Notice: Subject to any disclaimer, the term of this patent is extended or adjusted under 35 U.S.C. 154(b) by 0 days.

(21) Appl. No.: 13/035,352

(22) Filed: Feb. 25, 2011

(65) Prior Publication Data

US 2011/0244507 A1 Oct. 6, 2011

Related U.S. Application Data

(62) Division of application No. 12/242,962, filed on Apr. 16, 2009, now Pat. No. 7,919,582, which is a division of application No. 10/203,450, filed as application No. PCT/EP01/01424 on Feb. 9, 2001, now Pat. No. 7,538,197.

(60) Provisional application No. 60/248,224, filed on Nov. 15, 2000.

(30) Foreign Application Priority Data

Feb. 11, 2000 (DE) .................. 100 06 174
Feb. 11, 2000 (DE) .................. 100 06 175

(51) Int. Cl.
C07K 7/06 (2006.01)
C07K 14/475 (2006.01)
C07K 16/22 (2006.01)
G01N 33/53 (2006.01)

(52) U.S. Cl.
USPC .......... 435/7.1; 530/329; 530/387.1; 530/399

(58) Field of Classification Search
None
See application file for complete search history.

(56) References Cited

U.S. PATENT DOCUMENTS 5,530,109 A 6/1996 Goodearl et al.
5,763,213 A 6/1998 Ho et al.
5,854,220 A 12/1998 Goodearl et al.
6,147,190 A 11/2000 Goodearl et al.
2004/0191818 A1* 9/2004 O'Toole et al. .................. 435/6

FOREIGN PATENT DOCUMENTS

EP 1252186 10/2002
WO 92 20798 11/1992
WO WO-2009062750 A2 * 5/2009

OTHER PUBLICATIONS

Phillips, A.J. The challenge of gene therapy and DNA delivery. J Pharmacy Pharmacol 53: 1169-1174, 2001.*
Vidal et al. Making sense of antisense. Eur J Cancer 41: 2812-2818, 2005.*
Esper et al. Neuregulins: versatile growth and differentiation factors in nervous system development and human disease. Brain Res Reviews 51: 161-175, 2006.*
Halliday et al. Alzheimer's disease and inflammation: a review of cellular and therapeutic mechanisms. Clin Exp Pharmacol Physiol 27(1-2): 1-8, 2000.*
Steece-Collier et al. Etiology of Parkinson's disease: genetics and environment revisisted. Proc Natl Acad Sci USA 99(22): 13972-13974, 2002.*
Feigin et al. Recent advances in Huntington's disease: implications for experimental therapeutics. Curr Opin Neurol 15(4): 483-489, 2002.*
Malenka et al. Long-term potentiation—a decade of progress? Science 285: 1870-1874, 1999.*
Mahajan et al. Immunological assays for chemokine detection in in-vitro culture of CNS cells. Biol Proced Online 5(1): 90-102, 2003.*
Falls et al. Neuregulins: fuctions, forms, and signaling strategies. Exp Cell Research 284: 14-30, 2003.*
Pankonin et al. Differential distribution of neuregulin in human brain and spinal fluid. Brain Res 1258: 1-11, 2009.*
Eilam R. et al.: "Activity-dependent regulation of Neu Differentiation Factor/Neuregulin expression in rat brain" Proceedings of the National Academy of Sciences of the USA, vol. 95, Feb. 1998, pp. 1888-1893, XP002187768; abstract; p. 1890; figure 2 p. 1889; figure 1; p. 1892; figure 5.
Wen D. et al.: "Structural and functional aspects of the multiplicity of Neu Differentiation Factors" Molecular and Cellular Biology, vol. 14, No. 3, Mar. 1994, pp. 1909-1919, XP002064746; ISSN: 0270-7306; abstract; p. 1912; figure 1.
Chew Li-Jin and Gallo V.: Regulation of ion channel expression in neural cells by hormones and growth factors: Molecular Neurobiology, vol. 18, No. 3, Dec. 1998, pp. 175-225, XP001053101; p. 194; table 2; p. 205-p. 206.
Raabe et al, GLIA, vol. 45, pp. 197-207, 2004.
Meyer et al., Development, vol. 124, pp. 3575-3586, 1997.
Wolpowitz et al., Cysteine-rich domain isoforms fo the Neuregulin-1 gene are required for maintenance of peripheral synapses, Neuron 25(1):79-91, 2000.
Schillo et al., "Integrative proteomics: Functional and molecular characterization of a particular glutamate-related neuregulin isoform" J Proteome Res 4: 900-908, 2005.
Burgess et al., "Biosynthetic Processing of *neu* Differentiation Factor", The Journal of Biological Chemistry, vol. 270, No. 32, Issue of Aug. 11, pp. 19188-19196, 1995.
Lu et al., "Post-translational Processing of Membrane-associated *neu* Differentiation Factor Proisoforms Expressed in Mammalian Cells", The Journal of Biological Chemistry, vol. 270, No. 9, Issue of Mar. 3, pp. 4775-4783, 1995.

(Continued)

Primary Examiner — Bridget E Bunner
(74) Attorney, Agent, or Firm — Rothwell, Figg, Ernst & Manbeck, P.C.

(57) ABSTRACT

The invention relates, inter alia, to the use of neuregulin-β as an indicator in a method for detecting a neuronal process. The invention furthermore relates to the use of neuregulins, preferably a neuregulin isoform having an isoelectric point in the range from pH 4.3 to 5.0, as a target for detecting and/or exerting an influence on neuronal processes, in particular for exerting an influence on long-term memory. Neuregulins, in particular neuregulin-β and also substances which exert an influence on the status, i.e. the expression and/or post-translational modification, of neuregulin-β, can therefore be used as agents for controlling the course of, treating and/or alleviating neuronal diseases, e.g. Alzheimer's disease.

4 Claims, 4 Drawing Sheets

(56) References Cited

OTHER PUBLICATIONS

Ben-Baruch et al., "Neu Differentiation Factors: A Family of Alternatively Spliced Neuronal and Mesenchymal Factors (43746)", P.S.E.B.M., vol. 206, pp. 221-227, 1994.

Okazi et al., "Neuregulin-β induces expression of an NMDA-receptor subunit", Nature, vol. 390, Dec. 18-25, 1997, pp. 691-694.

Chew et al., "Regulation of Ion Channel Expression in Neural Cells by Hormones and Growth Factors", Molecular Neurobiology, vol. 18, 1998, pp. 175-225.

Ho et al., "Sensory and Motor Neuron-derived Factor", The Journal of Biological Chemistry, vol. 270, No. 24, Issue of Jun. 16, pp. 14523-14532, 1996.

NiceProt View of Swiss-Prot: Q15491, Oct. 9, 2004.

Lu et al., "Studies on the Structure and Function of Glycosylated and Nonglycosylated *neu* Differentiation Factors", The Journal of Biological Chemistry, vol. 270, No. 9, Issue of Mar. 3, pp. 4784-4791, 1995.

\* cited by examiner

SEQUENCE LISTING

<160> NUMBER OF SEQ ID NOS: 11

<210> SEQ ID NO 1
<211> LENGTH: 5
<212> TYPE: PRT
<213> ORGANISM: Rattus norvegicus

<400> SEQUENCE: 1

Met Ser Glu Arg Lys
1               5

<210> SEQ ID NO 2
<211> LENGTH: 6

```
<212> TYPE: PRT
<213> ORGANISM: Rattus norvegicus

<400> SEQUENCE: 2

Gly Lys Gly Lys Lys Lys
1               5

<210> SEQ ID NO 3
<211> LENGTH: 6
<212> TYPE: PRT
<213> ORGANISM: Rattus norvegicus

<400> SEQUENCE: 3

Gln Lys Leu His Asp Arg
1               5

<210> SEQ ID NO 4
<211> LENGTH: 7
<212> TYPE: PRT
<213> ORGANISM: Rattus norvegicus

<400> SEQUENCE: 4

Ile Gln Lys Lys Pro Gly Lys
1               5

<210> SEQ ID NO 5
<211> LENGTH: 7
<212> TYPE: PRT
<213> ORGANISM: Rattus norvegicus

<400> SEQUENCE: 5

Asn Lys Pro Glu Asn Ile Lys
1               5

<210> SEQ ID NO 6
<211> LENGTH: 8
<212> TYPE: PRT
<213> ORGANISM: Rattus norvegicus

<400> SEQUENCE: 6

Ala Glu Glu Leu Tyr Gln Lys Arg
1               5

<210> SEQ ID NO 7
<211> LENGTH: 10
<212> TYPE: PRT
<213> ORGANISM: Rattus norvegicus

<400> SEQUENCE: 7

Tyr Gly Val Ser Gly Tyr Pro Thr Leu Lys
1               5                   10

<210> SEQ ID NO 8
<211> LENGTH: 16
<212> TYPE: PRT
<213> ORGANISM: Rattus norvegicus

<400> SEQUENCE: 8

Ala Ser Leu Ala Asp Ser Gly Glu Tyr Met Cys Lys Val Ile Ser Lys
1               5                   10                  15

<210> SEQ ID NO 9
<211> LENGTH: 22
<212> TYPE: PRT
<213> ORGANISM: Rattus norvegicus
```

-continued

```
<400> SEQUENCE: 9

Asp Arg Gly Ser Arg Gly Lys Pro Gly Pro Ala Glu Gly Asp Pro Ser
1               5                   10                  15

Pro Ala Leu Pro Pro Arg
            20

<210> SEQ ID NO 10
<211> LENGTH: 18
<212> TYPE: PRT
<213> ORGANISM: Rattus norvegicus

<400> SEQUENCE: 10

Trp Phe Lys Asn Gly Asn Glu Leu Asn Arg Lys Asn Lys Pro Glu Asn
1               5                   10                  15

Ile Lys

<210> SEQ ID NO 11
<211> LENGTH: 23
<212> TYPE: PRT
<213> ORGANISM: Rattus norvegicus

<400> SEQUENCE: 11

Lys Asp Arg Gly Ser Arg Gly Lys Pro Gly Pro Ala Glu Gly Asp Pro
1               5                   10                  15

Ser Pro Ala Leu Pro Pro Arg
            20
```

USE OF NEUREGULIN-β AS AN INDICATOR AND/OR TARGET

This application is a divisional of U.S. application Ser. No. 12/242,962 filed Apr. 16, 2009, now U.S. Pat. No. 7,919,582, which is a divisional of U.S. application Ser. No. 10/203,450 filed Aug. 9, 2002, which issued as U.S. Pat. No. 7,538,197 on May 26, 2009, which is a 35 U.S.C. 371 National Phase Entry Application from PCT/EP2001/01424, filed Feb. 9, 2001, which is a non-provisional of U.S. Application No. 60/248,224 filed Nov. 15, 2000, claims the benefit of German Patent Application Nos. 100 06 175.3 and 100 06 174.5 filed on Feb. 11, 2000, the disclosure of which are incorporated herein in their entirety by reference.

The invention relates to the use of neuregulin-β as an indicator and/or target in a screening method for identifying active compounds. The invention, furthermore relates to the use of neuregulins, preferably a neuregulin isoform having an isoelectric point in the region of pH≤7, in particular from pH 4.3 to 5.0, as a target for detecting and/or exerting an influence on neuronal processes, in particular for exerting an influence on long-term memory. Neuregulins, in particular neuregulin-β and also substances which exert an influence on the status, i.e. the expression and/or post-translational modification, of neuregulin-β can therefore be used as agents for controlling the course of, treating and/or alleviating neuronal diseases, e.g. Alzheimer's disease.

Neuregulins (also ARIA, neurogenic differentiation factors, heregulins and DDF) belong to a family of widely distributed and known growth and differentiation factors. For example, the publication by Ozaka M. et al., Nature 1997, December 10-25, 390(6661): 691-4 describes the influence of neuregulin-β in inducing expression of the NR2C subunit of the NMDA receptor.

WO99/18976 describes methods for the treatment and/or prophylaxis of neurological diseases, which methods comprise administering a neuregulin, or a fragment or derivative of a neuregulin, or a nucleic acid encoding a neuregulin or a neuregulin fragment or derivative, to a patient. Only investigations at the genetic level are carried out in WO99/18976. Since modifications at the transcript level and/or protein level can result in the formation of more than 100 different molecular protein species from a single gene, the information given in WO99/18976 is not sufficient for being able to identify those protein species which are in fact relevant for neurological processes.

WO98/55611 describes the use of a 15 bp-long neuregulin response element in therapeutic methods and screening methods for identifying active compounds.

The techniques of proteome analysis were introduced some time ago. The term "proteome" is to be understood as meaning the entirety of all the proteins which are expressed in a cell, a tissue or an organism (see: "From Genome to Proteome" by Michael J. Dunn, 2000, Wiley/VCH, Weinheim; "Proteome Research, Two-Dimensional Gel-Electrophoresis and Identification Methods" by Thierry Rabilloud, 2000, Springer-Verlag, Berlin; see also: "Proteome Research: New Frontiers in Functional Genomics" by Marc R. Wilkins et al., 1997, Springer-Verlag, Berlin). The techniques of proteome analysis are 2-D-PAGE (two-dimensional gel electrophoresis) for fractionating the individual proteins in a complex biological sample and methods of mass spectrometry, in particular MALDI-TOF-MS (matrix-assisted laser desorption ionization time of flight mass spectrometry) and ESI-MS (electro spray ionization mass spectrometry) (see: "Mass Spectrometry: Principles and Applications", Edmond De Hoffmann, Jean Charette, Vincent Stroobant, Jul Trottier (August 1996), John Wiley & Sons, ISBN: 0471966975).

U.S. Pat. No. 5,721,135 describes methods and devices for identifying biologically active substances and their effect on living cells. U.S. Pat. No. 5,089,385 describes a method for culturing cells in a flow through cell cultivation system. U.S. Pat. No. 5,134,062 describes a method for diagnosing neuronal abnormalities and for identifying potential therapeutic active compounds for treating them. DE-OS 19735926 describes an arrangement for measuring the intrinsic NADH fluorescence of cell cultures. WO90/05179 discloses a perfusible cell culture device for expanding and culturing biological cells.

Whereas the appropriate analytical techniques can probably be regarded as being fully matured in the field of genomes, in the field of proteomes there is still a lack of techniques which make it possible, aside from actually analyzing proteins and their fragments, also to record the complex chronological courses of the very wide variety of actions and interactions which take place in connection with physiological processes, including recording them in a chronologically resolved manner, and consequently to draw conclusions with regard to the actual physiological processes and the underlying interactions and their partners. In this way, it was possible to test pharmaceutical active compounds selectively.

In this connection, the following is understood, according to the invention, by the term "effect space analysis/effector space analysis":

An effect space is defined by a coordinate system in which each coordinate represents the possible sizes or amplitudes of an effect, for example the possible concentrations of the intracellular calcium, which can be achieved in a nerve cell under physiological and pathophysiological conditions. All the effects which are to be taken into consideration then form the effect space; in the case of three possible effects, such an effect space is three-dimensional; in the case of n effects, it is n-dimensional. The same applies for considering the concentrations of effectors, e.g. neurotransmitters, etc. The "effect space analysis/effector space analysis" integrates experimental determinations/measurements regarding the conditions of effects and effectors in a given system with regard to the transition, which is medically/physiologically of interest, between effect space and effector space, which transition is defined by affinities, reaction parameters, transport parameters and other kinetic parameters.

When active compounds are being screened, at least one parameter, that is an indicator or a target, is required for the observed effect space of a cell system in order to make the screening possible as such. In addition to this, however, it is also possible, independently thereof, or as what is more or less a preliminary step to the screening, to determine also indicators and/or targets by means of correlation analysis by precise observation and evaluation of the individual results. Within the meaning of the invention, indicators denote substances which constitute a parameter in an effect space since they become actively evident, for example by means of a change in concentration, in physiological processes which are to be investigated, and consequently, being more or less visible and effect space-bound and/or system-bound, do in fact constitute an indicator. In general, the cell systems to be investigated are stimulated with a particular substance, for example with glutamate, after which the results are recorded and correlated with each other and, where appropriate, new indicators are discovered. In this connection, the indicators are as a rule not directly connected causally with the stimulations but, rather, indirectly by way of several steps. According to the invention, the term target denotes substances which constitute a parameter in an effect space since they become actively evident, for example by means of a change in concentration, in physiological processes which are to be investigated and consequently, being more or less visible and effect space-bound and/or system-bound, do in fact constitute a special type of indicator. In general, the cell systems which are to be investigated are stimulated with a particular substance, for example with glutamate, after which the results are recorded and correlated with each other and, where appropriate, these new special indicators are discovered. In this connection, these special indicators, namely the targets, are not as a rule indirectly connected causally, by way of several steps, with the stimulations, as in the case of the actual indicators, but, instead, directly connected causally. Consequently, each indicator is potentially a target and vice versa; this of course depends on the cell system to be investigated and on the effect space.

A problem of the present invention is therefore to provide such a target structure in a screening method for active compounds. Another problem of the present invention is to find novel targets for exerting an influence on neuronal processes.

These problems are solved by the subject-matter of the application. Initially, according to the invention, it is a matter of using neuregulin-β as an indicator and/or target in a screening method for identifying active compounds, in particular active compounds for exerting an influence on neuronal processes. It was surprisingly possible to show that neuregulin-β can be used as an indicator and/or target in such a screening method. The screening method can be used for active compounds for exerting an influence on changes in calcium concentration (calcium is understood here to mean $Ca^{2+}$) which are mediated by glutamate receptors, and be used for gathering multidimensional performance data for the effect space/effector space analysis of active compounds.

Furthermore, according to the invention, it is the matter of using neuregulin-β as an indicator and/or target in methods for detecting, and/or exerting an influence on, neuronal processes. In this connection, the use as a target involves modulating activity, quantity and/or molecular status with regard to post-translational modifications (PTMs) of neuregulin-β in a target cell, for example a target tissue or target organ. The target cells are preferably neuronal cells.

Finally, the invention also relates to novel neuregulin-β isoforms, for example PTM variants which exhibit isoelectric points of pH≤7 and, particularly preferably, isoelectric points in the pH range between 4.3 and 5.0, particularly between pH 4.5 and 4.7. These novel neuregulin-β isoforms and PTM variants are of particular importance for neuronal processes.

In the method for collecting multidimensional performance data for the effect/effect space analysis of active compounds, cell culture systems, which have been introduced into a flow cell device and applied to substrates, are initially incubated with labeling substances which are in each case suitable, for example fluorescent dyes, and/or with isotopic mixtures of different elements. Subsequently, the cell culture systems are stimulated and the fluorescence signals which result in dependence on the stimulation conditions are detected, directly in the cell culture system, in a chronologically synchronous and time-resolved manner, and/or the isotopic mixtures are detected in the perfusate in a time-resolved manner, and/or the isotopic mixtures are detected directly in the cell culture systems in a time-integrated manner, with the perfusate being subjected to a synchronized fractionation and continuing analysis, proteins which are present in the cell culture systems and which change under the chosen conditions and/or behave specifically being characterized and identified, and the multidimensional performance data which had been obtained for the effect space/effector space analysis of active compounds finally being integrated.

This above-described method for performing the effect space/effector space analysis, and devices which are suitable for implementing the method, are also in general form, i.e. not in connection with neuregulin, an independent invention and consequently part of the subject-matter of the present application.

According to the invention, the terms "LTP" and "LTD" are to be understood as meaning "long-term potentiation" and "long-term depression". It was surprisingly possible to demonstrate that neuregulin-β participates directly in neuronal long-term processes, which participation is mediated by way of the NMDA receptors, by means of glutamate-induced changes in the intracellular concentrations of calcium (general literature references: Anwyl R., "The role of amino acid receptors in synaptic plasticity", in: Cortical plasticity, LTP and LTD (Fazeli M. S. & Collingride G. L. eds.) Bios. Scientific Publishers, Oxford, 9-28 (1996); Cormier, R. J., Mauk, M. D. & Kelly, P. "Glutamate iontophoresis induces long-term potentiation in the absence of evoked presynaptic activity", Neuron 10, 907-919 (1993); Malgaroli, A. & Tsien, R. W. "Glutamate-induced long-term potentiation of the frequency of miniature synaptic currents in cultured hippocampal neurons", Nature 357, 134-139 (1992); Soskiv-V, Gorlach M., Poznanovic S., Boemhmer F. D., Godovac-Zimmermann J., "Functional proteomics analysis of signal transduction pathways of the platelet-derived growth factor beta receptor", Biochemistry 38, 1757-64 (1999); Wong et al., "The anticonvulsant MK-801 is a potent NMDA antagonist", Proc. Natl. Acad Sci USA 83, 7104-7106 (1986)).

An essential feature of the invention is the fact that it has only, for the first time, become possible, and surprisingly only by specifically and synchronously interconnecting the above-mentioned operational steps, to ensure that the high demands placed on the reproducibility of the analytical techniques to be employed for such cell systems to be investigated are met (the systems are chaotic). Employing the individual analytical steps consecutively would not lead to the desired, utilizable results.

In the first place, it is advantageous if neuregulin-β is used as an indicator and/or target for exerting an influence on LTP, LTD, epileptiform and/or epileptogenic events and/or excitation-toxic phenomena, since it is evident from the results given below that neuregulin-β is a characteristic key factor in the memory-relevant physiological phenomena LTP/LTD.

It is advantageous if the cell culture systems are cultured on microscope slides, which are then to be used in the flow cell device, since this is the only way to ensure that the cells are supplied to the performance tests as rapidly as possible, in an intact state and without any cells becoming detached.

It is furthermore advantageous if the cell culture systems which have been introduced into the flow cell device are first of all characterized microscopically in order to verify the basal requirements for further functional applications.

The microscopic characterization is advantageously a morphological characterization in a phase contrast microscope or a video-microscopic recording of cell behavior under the influence of various physical parameters and/or in dependence on the substrates, since said parameters are best for allowing the intactness and viability of the cells to be assessed rapidly.

When fluorescent labels are being used, the incubation is advantageously carried out, since tried and tested in practice, using Fura-2, Indo-1, Bis-Fura-2, Quin-2 and derivatives, Mag-Fura-2, Mag-Fura-5 and/or Mag-Indo-1 as the fluorescent dye. In addition to this, it is also possible to use other fluorescent dyes, such as anthracene-9,10-dipropionic acid. The names which are mentioned first are trivial names for well known fluorescent dyes, which are also listed in the Handbook of Fluorescent Probes and Research Chemicals, 6$^{th}$ edition, R. P. Haugland, 1996, Molecular Probes, Eugene, Oreg., USA.

When isotopic labels are being used, the incubation is advantageously carried out using an isotopic mixture in the form of ions or compounds of at least one of the elements hydrogen, calcium, magnesium, zinc, manganese, selenium, copper, cadmium, cobalt, carbon, nitrogen, iron, oxygen, sulfur and phosphorus, since these elements are the most important elements occurring in living systems.

It is advantageous if the stimulation is carried out using ligands of glutamatergic, GABA-ergic or cholinergic ligands, since these ligands have proved their value in practice. It is furthermore possible to conceive of using ligands for serotonin, catecholamine, opioid, melatonin or peptide receptors, voltage-regulated ion channels, and transport systems for neurotransmitters, ions and metabolites. Agonists which may in particular be mentioned are acetylcholine and nicotine.

It is furthermore advantageous if the time-resolved detection of the isotopic mixtures in the perfusate is carried out using ICP-MS and/or the time-integrated detection of the isotopic mixtures is carried out using ICP-MS, since, on the one hand, it is possible to measure the concentrations of any elements simultaneously and extremely sensitively, and, on the other hand, when suitable and stable isotopic markers are used, it is possible to analyze compartment-specific distributions of particular elements/ions.

In addition, the continuing analysis of the perfusate is advantageously carried out using fluorescence HPLC and/or using enzyme-coupled columns and/or electrochemically or fluorometrically (see, in this regard: Klapproth H., Reinheimer T., Metzen J., Munch M., Bittinger F., Kirkpatrick C. J., Hohle K. D., Schemann M., Racke K., Wessler I., 1997, Non-neuronal acetylcholine, a signaling molecule synthesized by surface cells of rat and man, Naunyn Schmiedebergs Arch Pharmacol., 355(4): 515-23; or Rieny J., Tucek S., Vins I., 1992, Sensitive method for HPLC determination of acetylcholine, choline and their analogues using fluorometric detection, J. Neurosci Methods, 41(1): 11-17) and/or mass-spectrometrically, for example using EI-MS (electron impact ionization mass spectrometry; samples are ionized by means of an electron beam), FAB-MS (fast atom bombardment mass spectrometry: samples are ionized by being bombarded with inert gas atoms), FD-MS (field desorption mass spectrometry; under the influence of high electric fields, positive ions are desorbed from a wire, onto which a solid sample is applied, and then analyzed), MALDI-TOF-MS and ESI-MS, since these methods have proved to be of value in practice.

It is advantageous if fluorescent labels are used for derivatization when analyzing the perfusate and the labels are subsequently identified and quantified by means of HPLC using a fluorescence detector since this makes it possible to achieve the high levels of sensitivity which are required for detecting the substances in question (1-50 femto mol) in the relatively small volumes of the flow cell device in one operational procedure.

The following embodiments have advantageously proved themselves to be of value in practice:
when amino acids are being analyzed, they are derivatized with o-phthaldialdehyde and 2-mercaptoethanol under alkaline conditions and subsequently identified. Alternatively, amino acids can also be derivatized by being derivatized with other reagents, such as 6-aminoquinolyl-N-hydroxysuccinimidylcarbamate or other carbamates or phenylisothiocyanates (cf., e.g. Bidlingmeyer et al., J. Chromatogr. 336 (1984), 93-104; Iwaki et al., J. Chromatogr. 407 (1987), 273-279; Cohen and Styrdom, Anal. Biochem. 174 (1988), 1-16; Cohen et al.: "Compositional Protein Analysis Using 6-Aminoquinolyl-N-Hydroxysuccinimidyl Carbamate, a Novel Derivatization Reagent", in: Techniques in Protein Chemistry IV, R. H. Angeletti, Ed. (1993), Academic Press, San Diego, Calif.; Styrdom and Cohen: "Sensitive Analysis of Cystine/Cysteine using 6-Aminoquinolyl-N-Hydroxysuccinimidyl Carbamate (AQC) Derivatives", in: Techniques in Protein Chemistry IV, R. H. Angeletti, Ed. (1993), Academic Press, San Diego, Calif.).

When catecholamines are being analyzed, they are preferably derivatized with benzylamine under the influence of potassium hexacyanoferrate to give fluorescent compounds, and subsequently identified. When acetylcholine and choline are being analyzed, they are preferably detected electrochemically using an enzyme-coupled column. When nucleotides, in particular adenine nucleotides, are being analyzed, they are preferably derivatized by reaction with chloroacetyldehyde and detected as etheno compounds.

Proteins which are present in the cell culture systems and which change under the chosen conditions and/or behave specifically are characterized and identified using 2-D-PAGE and MALDI-TOF-MS and/or ESI-MS, since these methods have proved to be of value in practice.

It is advantageous if all the measurements are carried out in a temperature-controlled manner, since changes in temperature of 0.5-1° C., in particular in the central nervous system, play an important physiological role (see: Kavanau, J. L., "Memory, sleep and the evolution of mechanisms of synaptic efficacy maintenance", 1997, Neuroscience, 79, 7-44).

In the method according to the invention, the cell growth and cell behavior can be analyzed on, and with regard to, supports which are used for the cell culture systems, such that it is advantageously possible to analyze all the properties of the support materials which are of interest, in particular in relation to artificial substitutes in implantation medicine or else in relation to the authenticity of cell culture systems as regards their respective disease-model or tissue-model character, and consequently validate the model systems employed.

Flow cell devices (from GlycoTech Corporation) which have a chamber height of approx. 150 μm, in particular, are known from the prior art; however, they are not suitable for the purposes of the invention.

A flow cell device according to the invention, in particular for use in methods for collecting multidimensional performance data for the effect space/effector space analysis of active compounds, having a base plate with a duct, an upper plate and a closure ring, is characterized by the fact that the chamber formed by the base plate, together with the duct and the overlying covering plate, is from 30 to 100 μm in height. The individually adjustable height of the chamber is advantageously to be achieved using bolts which are made, in particular, of metal or Teflon and which are to be sunk into at least one of the two plates (upper plate and base plate).

As a result of its specific design, such a flow cell device can be used to detect, for the first time, the release of transmitters, in particular low molecular weight transmitters, by neuronal cells. As a result of a particularly advantageous cell/volume ratio, it is surprisingly for the first time possible at all to achieve a physiological shearing rate of the fluid on the cells. Physiological shearing rates are those shearing rates which can arise, for example, in blood vessels or other biological cavities in which fluids in motion are present (0.1-5 Pa). As a result of the very highly pronounced laminarity of flow, uniform distributions of active compounds, and uniform conditions, are present at virtually all points in the flow-through device. In addition to this, it is also possible to lyse preparations directly.

Using this flow cell device, it is possible, for the first time, to meet the very high demands with regard to the sensitivity of the released substances such that it is possible to draw reliable conclusions with regard to concentrations of the substances (if the volumes were too large, the concentrations of the individual substances would be too low).

It is first of all advantageous if the height of the chamber in the flow cell device is from 30 to 50 μm since this thereby ensures a specimen distance which is optimal for microscopy with regard to high magnifications and large light yields. In addition, the small volume of the flow cell device prevents the substances released by the cells being diluted to too great an extent; in addition, this geometry results in a very favorable Reynolds number for laminar flow.

Advantageously, the supply and discharge lines are arranged virtually at the level of the flow channel in order to avoid turbulences.

Advantageously, the inner surfaces of the chamber are virtually planar in form since, in this way, it is possible to ensure uniform conditions with regard to pressure, shearing rates and the microscopy (adjustment of the levels).

Furthermore, the flow cell device additionally possesses a slide-receiving frame between the base plate and the upper plate in order to be able to receive standard slides. This ensures compatibility with automated laboratory devices for histology and/or immunocytochemistry.

The slide-receiving frame is made of metal in order, advantageously, to achieve the high degree of mechanical strength and joint rigidity and to enable sterilization to take place at $T \geq +100°$ C.

The flow cell device advantageously has an elastic gasket between the base plate and the upper plate since this ensures a defined distance and the fact that the chamber is leak-proof.

It is advantageous if the elastic gasket is composed of silicone, because this material is autoclavable under standard conditions and possesses neutral properties with regard to cell compatibility.

The base plate and/or upper plate is/are advantageously composed of polycarbonate since this material guarantees transparency (UV/Vis) for all the microscopic techniques which come into consideration.

In a proven manner, the flow cell device possesses several chambers, which are arranged virtually in parallel, for the purpose of testing several active compounds under exactly the same conditions as far as the cell populations are concerned.

The method according to the invention is particularly suitable for screening active compounds, in particular for identifying targets. The term "targets" is understood as meaning target structures. These are proteins or metabolites which have a decisive key function in a disease-relevant physiological process and which, for this reason, qualify particularly well as targets for attack by active compounds. Identifying a target makes it possible to carry out other screening methods for the purpose of identifying active compounds which are modulators, i.e. activators or inhibitors of the target.

In addition to this, the different supports for cell culture systems in the method according to the invention are suitable for analyzing the growth and behavior of the cells.

The device according to the invention for collecting multidimensional performance data for the effect space/effector space analysis of active compounds, in particular for implementing one of the above-described methods, comprises:
a flow cell device,
an arrangement for stimulating the cell culture systems,
an arrangement for directly detecting, in the cell culture systems, in a synchronous and time-resolved manner, fluorescence signals which result in dependence on the stimulation conditions, and/or an arrangement for detecting isotopic mixtures in the perfusate in a time-resolved manner and/or an arrangement for detecting isotopic mixtures directly in the cell culture systems in a time-integrated manner,
an arrangement for the synchronized fractionation and continuing analysis of the perfusate,
an arrangement for characterizing and identifying proteins which are present in the cell culture systems and which change under the selected conditions and/or behave specifically, and
an arrangement for integrating the resultant multidimensional performance data for the effect space/effector space analysis of active compounds.

Because of the above-described advantageous properties, it is advantageous if the device according to the invention exhibit a flow cell device of the above-described type.

The following forms have proved their value in practice and, for the reasons mentioned with regard to the method according to the invention, are to be regarded as being advantageous:

The arrangement for stimulating the cell culture systems is a computer-controlled administration system.

The arrangement for directly detecting, in the cell culture systems, in a synchronous and time-resolved manner, fluorescence signals which result in dependence on the stimulation conditions is a fluorescence spectroscopy arrangement.

The arrangement for detecting isotopic mixtures in the perfusate in a time-resolved manner is an ICP-MS arrangement (see, in this regard: ICP Spectrometry and its Applications, by Steve J. Hill (Editor), 2000, CRC Press, ISBN: 0849397391).

The arrangement for detecting isotopic mixtures directly in the cell culture systems in a time-integrated manner is an ICP-MS arrangement.

The arrangement for subjecting the perfusate to synchronized fractionation and continuing analysis exhibits a computer-controlled fraction collector and an HPLC arrangement having a fluorescence detector and/or an arrangement having enzyme-coupled columns and/or an arrangement having electrochemical or fluorometric detection and/or a mass spectrometer.

The arrangement for characterizing and identifying proteins which are present in the cell culture systems and which change under the chosen conditions and/or behave specifically comprises a 2-D-PAGE arrangement and a MALDI-TOF-MS arrangement and/or ESI-MS arrangement.

The arrangement for integrating the resultant multidimensional performance data for the effect space/effector space analysis of active compounds is a data base-assisted computer arrangement.

The arrangement for analyzing the growth and behavior of the cells on and with regard to supports used for the cell culture systems is a computer-assisted image analysis arrangement having a video microscope.

The results of the uses according to the invention can, of course, also be used as provisional results for diagnostic methods. The results consequently serve, more or less, as the basis for a decision on the further course of action, or determine the subsequent course within a particular diagnostic method.

The invention also relates to the use of neuregulin-β as an indicator in a method for detecting neuronal processes. This method is preferably a diagnostic method which comprises determining the presence, the concentration and/or the activity of neuregulin-β in a sample to be investigated (in-vitro diagnosis) or an organism to be investigated (in-vivo diagnosis). A diagnostic method of this nature can comprise, for example, a detection at the protein level, for example using antibodies, or a detection at the transcript level, for example using Northern Blots, reverse transcription and/or amplification processes. In principle, the skilled person is familiar with the implementation of diagnostic methods of this nature.

The invention furthermore relates to the use of neuregulin-β as a target in a method for exerting an influence on neuronal processes. This method can comprise altering, for example decreasing or increasing, the concentration and/or activity of neuregulin-β, preferably in the region of the brain, of the spinal cord and/or of the nerve cells. This method can comprise administering neuregulin-β inhibitors, for example antibodies or low molecular weight substances and/or administering neuregulin-β antisense nucleic acids, if a decrease in the concentration and/or activity of neuregulin-β is desired. On the other hand, neuregulin-β or a nucleic acid encoding it can be administered to a target site in the organism if an increase in the quantity and/or activity of neuregulin-β is desired. Neuregulin-β can be administered in free form or associated with a suitable carrier, for example with vehicles such as micelles, liposomes, etc. Neuregulin-β-encoding nucleic acids can be administered in the form of what is termed "naked" DNA or in the form of vehicles, as previously specified, or, alternatively, in the form of viral vectors, e.g. adenoviruses, retroviruses, etc.

Alternatively, or in addition, it is also possible to administer substances which exert an influence on the expression and/or status of neuregulin-β. Such substances, e.g. inhibitors or activators, can readily be identified by means of the effect space/effector space analytical method according to the invention or by using other screening methods. The invention therefore also encompasses such substances, e.g. low molecular weight active compounds and/or biological substances, e.g. macromolecules such as proteins and nucleic acids, etc., and substances which are derived therefrom by means of modifications, and also their use in diagnostic and therapeutic methods.

In a preferred embodiment of the diagnostic and therapeutic methods, a detection takes place, or an influence is exerted on neuronal diseases, in particular neuronal degenerative diseases such as Alzheimer's disease. Thus, it is possible to conceive, for example, of a use in controlling the course of neuronal degenerative diseases. Thus, it has surprisingly been found that the nerve cells of patients suffering from Alzheimer's disease exhibit an overall reaction with anti-neuregulin-β antibodies which is more weakly positive than in the case of normal individuals.

Finally, the invention relates to novel neuregulin-β isoforms, e.g. PTM modifications, having an acid isoelectric point, preferably in the pH range from 4.3 to 5.0. The neuregulin isoform according to the invention has an apparent molecular mass (SDS-PAGE) of about 32 kD and, after stimulation in the effect/effect space analytical method according to the invention, appears in substantially larger quantities than without stimulation or in the case of controls. As demonstrated by mass-spectroscopic analysis, the protein contains peptide part fragments corresponding to peptides 81 to 87 and 88 to 94 of neuregulin-β. In addition to the protein having a complete sequence, the invention also covers physiologically active derivatives and fragments thereof. Such derivatives and fragments can be obtained by recombinantly expressing corresponding, mutagenized nucleic acid sequences or by means of proteolytic cleavage.

The neuregulin-β isoforms according to the invention can be isolated from mammalian neuronal cells, e.g. rat cells or human cells, using known methods, for example immunoadsorption using suitable antibodies, where appropriate in combination with an isoelectric fractionation.

The following examples and figures serve to clarify the invention.

BRIEF DESCRIPTION OF THE DRAWINGS

FIG. 1 is an aspect of a flow cell device according to the invention. A base plate (1) has a duct (2). A closure ring (4) lies centrosymmetrically on the base plate (1). In addition, a slide-receiving frame (7) can be seen lying on the base plate (1).

FIG. 2 is a cross section of a flow cell device shown in FIG. 1. In addition to the abovementioned features, the following can also be seen in FIG. 2: the closure ring (4) clamps the base plate (1) and an upper plate (3) together in a sealing manner using a silicone gasket (8). Bolts (not detailed) which are sunk into each of the plates (1, 3) ensure that the plates are a certain distance apart, thereby establishing a chamber height. The duct (2), which is now closed from above by means of the upper plate (3), forms a chamber, i.e. the actual chamber in which the interactions take place between cell cultures and flow media which flow in and out by way of supply lines and discharge lines (5, 6).

FIG. 3 is an aspect of an other flow cell device. A total of three ducts (2) are shown diagrammatically in this device.

FIG. 4 shows a 2-D-PAGE of glutamate-induced changes in hippocampal proteins. Hippocampal cells were stimulated with stimulation buffer (in mM): NaCl (125), KCL (5), $CaCl_2$ (2-6), $MgCl_2$ (0.8) glucose (5-10), HEPES (20), L-glutamate (0.01-0.1), glycine (0.01), bicucullin (0.01), pH 7.2; (A=control, B=glutamate, C=glutamate+MK-801; MK-801 is a specific glutamate receptor antagonist). In this connection, the measured or control quantity indicative of performance was a fluorescence signal measured using Fura-2, which signal is proportional to the calcium concentration (all the substances can be found in chemical catalogues supplied by Torris or Sigma).

The most striking and most consistent change is indicated by an arrow: Neu-β (32 kDa, pI=4.5 to 4.7 (isoelectric point)) can be observed in substantially larger quantity in the stimulated condition and is only weakly present, or cannot be found at all, in the controls.

Figure 1:
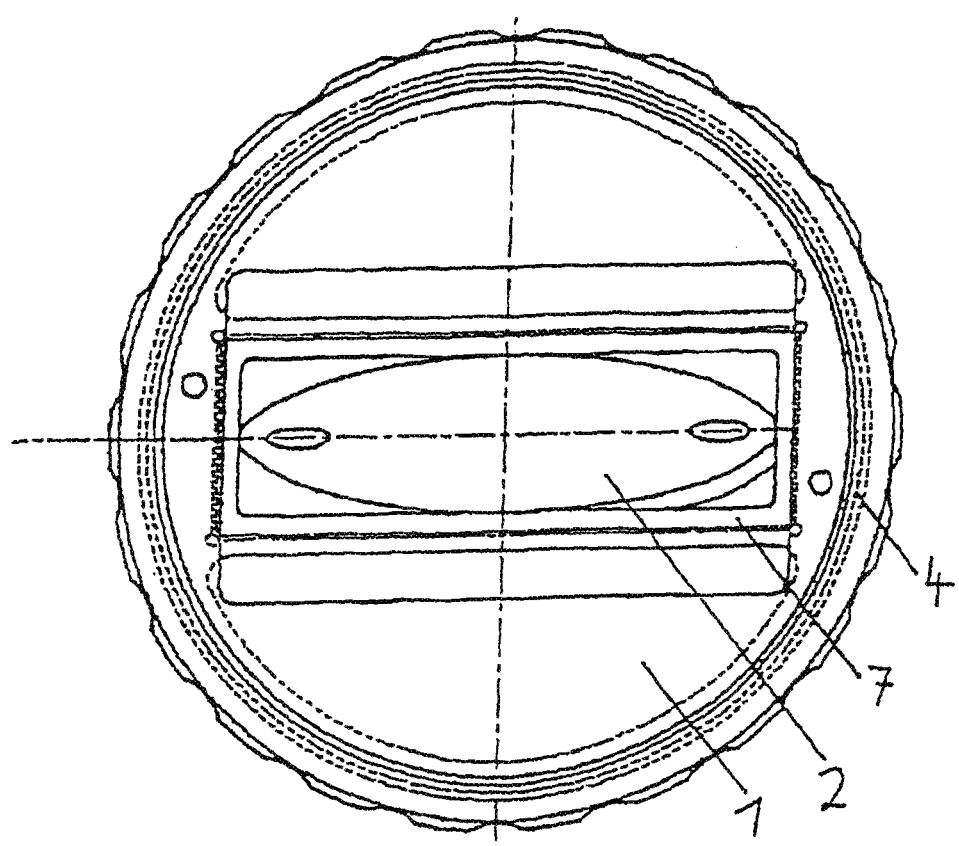
FIG. 1 shows an aspect of a flow cell device according to the invention.
Figure 2:
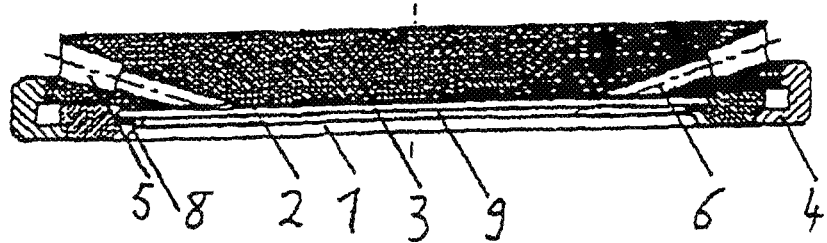
FIG. 2 shows a cross section of a flow cell device shown in FIG. 1
Figure 3:
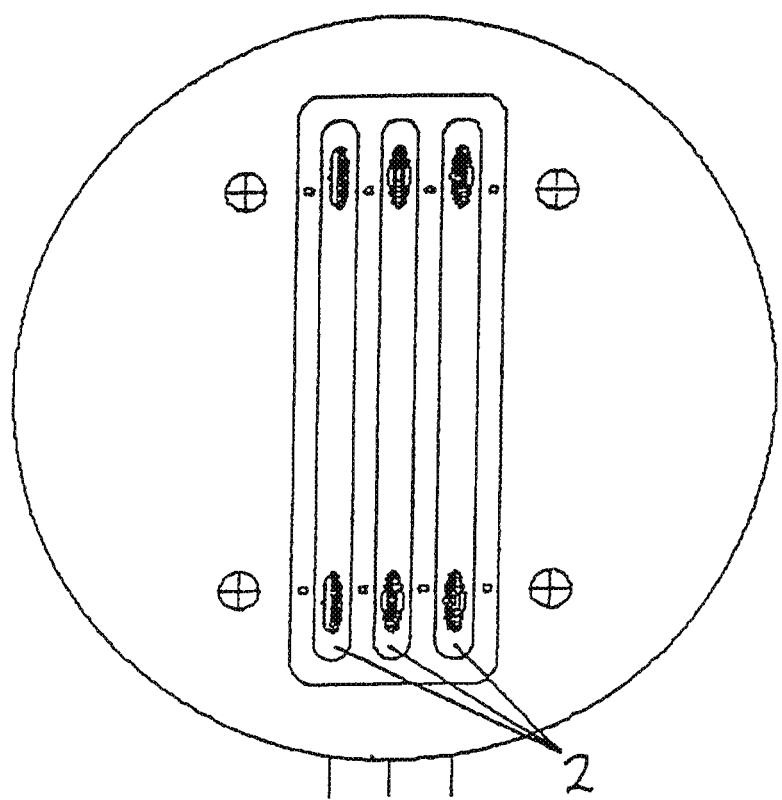
FIG. 3 shows an aspect of another flow cell device.
Figure 4:
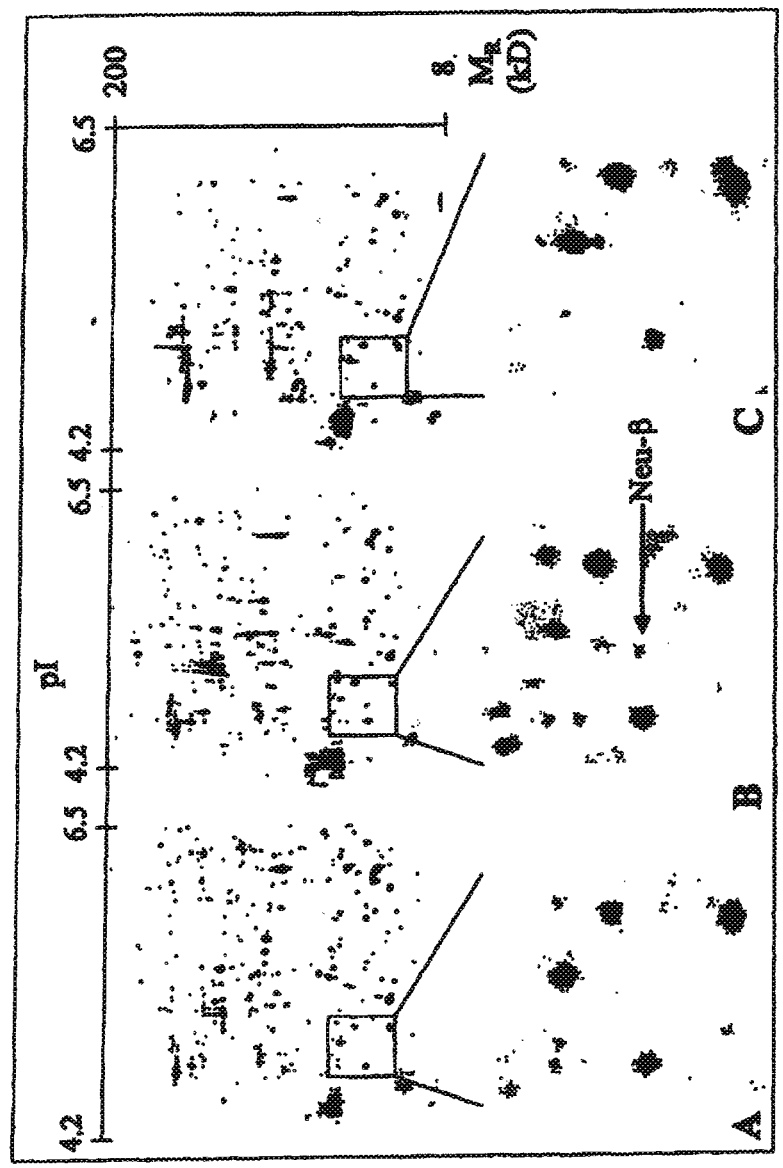
FIG. 4 shows a 2-D-PAGE of glutamate-induced changes in hippocampal proteins.
Figure 5:
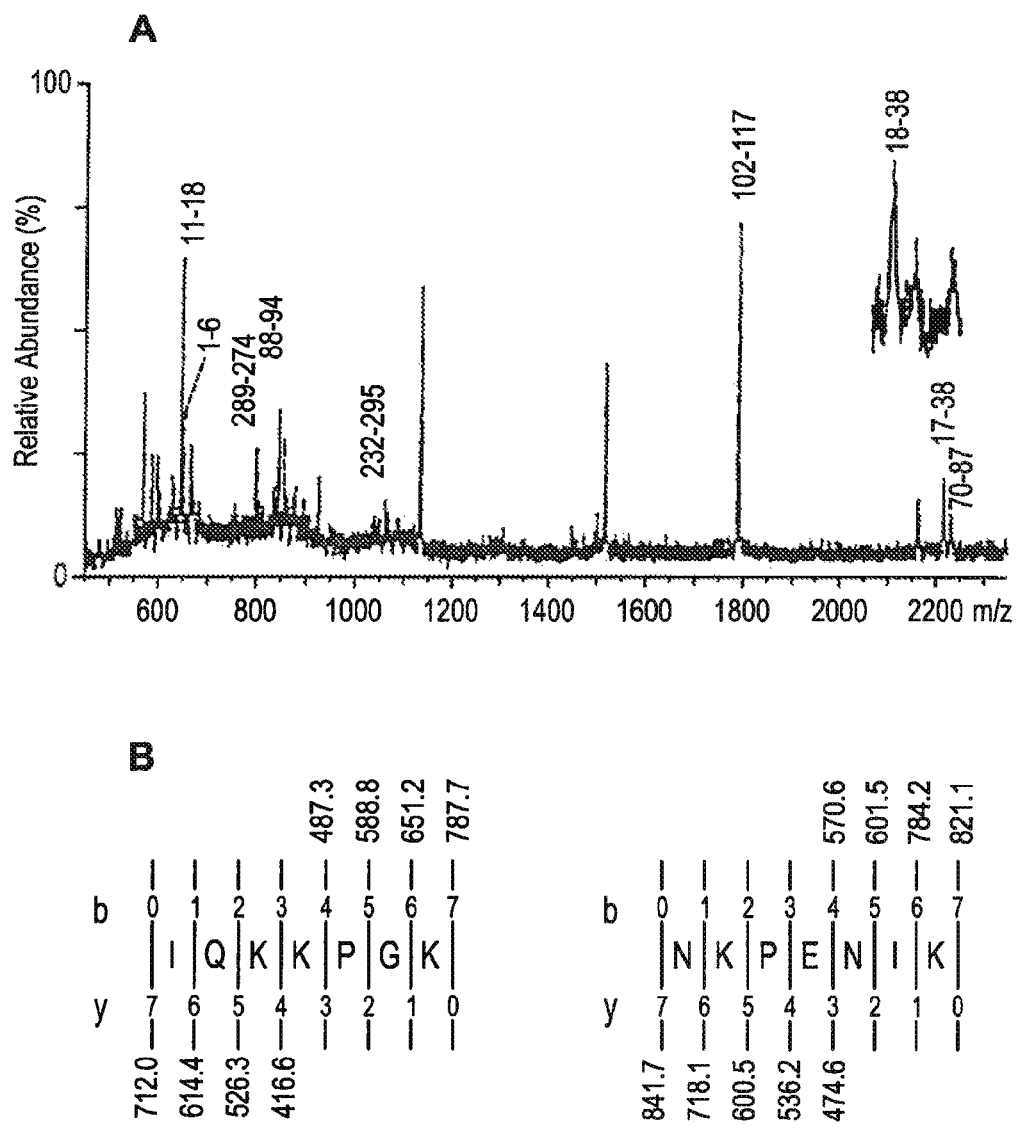
FIGS. 5A and 5B show the use of ESI-MS to identify neuregulin-β by means of MS/MS analysis.

FIGS. 5A and 5B show the use of ESI-MS to identify neuregulin-β by means of MS/MS analysis.

Selected peptides from the MALDI-MS were fragmented for amino acid sequencing by ESI-MS. (MALDI, ESI sequencing as in Soskic V., Görlach M, Poznanovic S., Boehmer F D, Godovac-Zimmermann J., "Functional proteomics analysis of signal transduction pathways of the platelet-derived growth factor beta receptor" (1999), Biochemistry 38, 1757-1764; or "Proteome Research, Two-Dimensional Gel Electrophoresis and Identification Methods" by Thierry Rabilloud, 2000, Springer-Verlag, Berlin). The sequences which are obtained unambiguously identify a neuregulin-β (details, see Table 2) FIG. 5(B): left sequence [SEQ ID NO: 4]; right sequence [SEQ ID NO: 5].

EXAMPLE 1

Identifying Neuregulin-β as an Indicator or Target for Neuronal Processes 1.1 Culture of Neuronal Cells (from Rat Hippocampus), LTP/LTD:

Suitable cell culture systems, in the case of neuregulin-β hippocampal primary cultures obtained from prenatal or neonatal rats (described in, for example, "Rat hippocampal neurons in low-density culture", K. Goslin, H. Asmussen, G. Banker; in "Culturing Nerve Cells, $2^{nd}$ edition 1998, pp. 339 ff; K. Goslin and G. Banker, eds. MIT Press, Cambridge, Mass., USA), are cultured on the above-described slides, introduced into the flow cell and initially characterized microscopically (morphological micrographs, etc. in the phase contrast microscope).

The cells are then incubated with fluorescent dyes which are in each case suitable (in the case of the memory-relevant experiments on neurons which have lead to the discovery of the special function of neuregulin-β: Fura-2, which is a calcium-sensitive fluorescent dye).

1.2 Effect Space/Effector Space Analysis

After that, the cells are stimulated using the computer-regulated administration system (in the case of the memory-relevant experiments on neurons which have lead to the discovery of neuregulin-β: 100 μm glutamate for 30 seconds).

The fluorescence signals in a larger number of cells are detected, in a time-resolved manner, in dependence on the stimulation conditions (temperature, active compound). In connection with neuregulin-β, glutamate induces an inflow of calcium ions, which inflow can be quantified very sensitively by way of the interaction with Fura-2.

Almost in parallel to this, the perfusate is subjected to a synchronized fractionation and analysis; in the case of hippocampal neurons, of neurotransmitters, by means of HPLC using fluorescence detection, in the case of other low molecular weight extracellular components, by means of EMI-MS, and in the case of stable isotopic tracers and metal ions, by means of ICP-MS.

In addition to this, for the purpose of further characterization, it is possible to carry out an immune staining of the cells using specific antibodies directed against surface markers.

Furthermore, proteins which change under the chosen experimental conditions, or otherwise behave in a conspicuous manner, are characterized and identified using the techniques of proteome research, namely by means of two-dimensional gel electrophoresis, MALDI-TOF-MS and ESI-MS.

Finally, the multidimensional performance data which have been obtained for the effect space/effector space analysis of active compounds are integrated, i.e. combined. The effect space/effector space analysis is a correlation analysis regarding individual processes and the changes in the concentration of particular substances accompanying them.

In the above-described set up, the following parameters were determined simultaneously or in an explicitly correlating manner. The increase in the inflow of calcium into neurons of hippocampal origin (proof of the neuronal identity by tau protein-staining the same cells after the functional part of the experiment) while the temperature remains the same identifies the physiological context (LTP(memory)-relevant). Accompanying this, are the simultaneous changes in the release of neurotransmitter (GABA), the influx of Mg into the cells, as detected using the stable isotopic tracer $^{26}$Mg. In particular, the appearance of neuregulin-β in the stimulated condition is a novel and unexpected result. This set of information has thereby been identified, for the first time, in a memory-relevant context. Neuregulin-β has consequently also been identified as a potential target for active compounds which are to be tested in relation to memory diseases. The setup which has been presented achieves a markedly higher information density than is achieved in conventional screening methods, which usually only investigate single parameters in connection with active compounds.

In the application example, the stable isotopic tracer is $^{26}$Mg. An anti-tau antibody (obtainable, for example, from SIGMA) was used for the immune staining.

Neuregulin-β was identified by means of two-dimensional PAGE using isoelectric focusing and employing immobilized, nonlinear pH gradients of from 3 to 10 and linear gradients of from 4 to 7 as the first dimension and SDS-PAGE (12% acrylamide) as the second dimension. Silver-staining the gels showed a reproducible pattern of several thousand proteins, with most of them remaining unchanged under all the conditions. The most conspicuous difference was a protein which had an apparent molecular mass of about 32 kD and a pI value of 4.5 to 4.7 and which, after stimulation, [lacuna] in substantially higher quantities than in the absence of stimulation or than in the controls (Addition of 10 μM MK-801, a specific inhibitor of NMDA receptors) (Wong et al, Proc. Natl. Acad. USA 83 (1986), at, 7104-7106).

The protein was excised from the gels, subjected to a trypsin cleavage within the gel and subsequently [lacuna] mass-spectroscopically by means of MALDI-TOF mass fingerprint and ESI peptide sequencing (Corthals et al., Identification of Proteins by Mass-Spectrometry, in: Proteome Research, Two-Dimensional Gel-Electrophoresis and Identification Methods, Thierry Rabilloud, Ed., Springer, Berlin (2000), 197-232).

The identity of the protein was confirmed by analyzing selected peptides by means of MS/MS analysis using ion traps, electrospray, mass spectroscopy of the peptide mixture, which was not fractionated and which had previously been analyzed by MALDI-TOF. The MS/MS analysis of m/z 798.4 was sufficient in order, inter alia, to identify the 88-94 peptide of neuregulin-β. The MS/MS analysis of m/z=842.7 confirmed the sequence of the peptide around position 81-87. These peptide sequences are conserved in the neuregulins α and β; however, neuregulins-β are predominant in the central nervous system (Meyer et al., Development 124 (1997), 3575-3586). The experimental conditions and the results are given in Tables 1 and 2.

While the pI calculated from the amino acid sequence of neuregulins is about 9.0, the neuregulin-β isoform identified in the present experiment has a pI in the range from 4.3 to 5.0, indicating the presence of extensive post-translational modifications.

The present results demonstrate that neuregulin-β is regulated by physiological activity and plays an important role in neural plasticity. It may furthermore be assumed that the NDF receptor tyrosine kinases ErbB-3 and ErbB4 are involved in the induction of LTP by way of neuregulin-β.

EXAMPLE 2

Identifying Neuregulin-β as a Target in Connection with Alzheimer's Disease

Section preparations (3 from patients with normal brain findings and 3 from patients suffering from Alzheimer's disease) were investigated immunohistochemically using the ABC method, with aminobenzidine serving as a substrate. The anti-neuregulin primary antibody (Santa Cruz Biotech) was tested out beforehand in two dilutions (1:10 and 1:100). As a negative control, a nonspecific goat serum was used in place of the primary antibody.

In the case of the preparations from normal brain, hippocampal structures were found which contained nerve cells which exhibited weak staining with the antibody in cytoplasm. Cells from the plexus choriodeus exhibited a reaction in the cytoplasm which was clearly positive.

Hippocampal structures containing nerve cells which exhibited a manifestly weaker reaction with the antibody in the cytoplasm were found in the brain tissue from patients suffering from Alzheimer's disease. Cells from the plexus choriodeus exhibited a more positive reaction in the cytoplasm.

Taken overall, the nerve cells from patients suffering from Alzheimer's disease appear to exhibit a reaction with anti-neuregulin-β antibodies which is more weakly positive than in the case of normal individuals.

TABLE 1

| Parameter | Concentration/ expression/ measured quantity (prestimulated) | Concentration/ expression/ measured quantity of the control | Method |
| --- | --- | --- | --- |
| GABA | 74 pMol | 87 pMol | fluorescence HPLC |
| Neuregulin-β | Strongly expressed | not expressed | 2-D PAGE, ESI-MS, MALDI-TOF-MS |

TABLE 1-continued

| Parameter | Concentration/ expression/ measured quantity (prestimulated) | Concentration/ expression/ measured quantity of the control | Method |
| --- | --- | --- | --- |
| $^{26}$Mg (intracellular) | 45 nM/mg of protein | 25 nM/mg of protein | ICP-MS |
| Calcium (intracellular) | 850 nM | 350 nM | Fura-2; fluorescence imaging |
| tau protein (neuronal marker) | positive | positive | Immuno staining with anti-tau antibody |
| Temperature | +22° C. | +22° C. | Intrinsic |

TABLE 2

MALDI Mass-spectrometric analysis of Neu-β Neu-β (*Rattus norvegicus*): 11 Peptides contain 35% (106/304 AS)

| Start | End | Expected Mass | Measured Mass | Sequence |
| --- | --- | --- | --- | --- |
| 1 | 5 | 650.3 | 650.8 | MSERK [SEQ ID NO: 1] |
| 11 | 16 | 645.4 | 644.9 | GKGKKK [SEQ ID NO: 2] |
| 269 | 274 | 796.4 | 796.0 | QKLHDR [SEQ ID NO: 3] |
| 88 | 94 | 798.5 | 798.4 | IQKKPGK [SEQ ID NO: 4] |
| 81 | 87 | 842.4 | 842.7 | NKPENIK [SEQ ID NO: 5] |
| 232 | 239 | 1036.5 | 1036.9 | AEELYQKR [SEQ ID NO: 6] |
| 94 | 103 | 1085.2 | 1085.0 | YGVSGYPTLK [SEQ ID NO: 7] |
| 102 | 117 | 1790.1 | 1790.7 | ASLADSGEYMCKVISK* [SEQ ID NO: 8] |
| 17 | 38 | 2214.1 | 2214.6 | DRGSRGKPGPAEGDPSPALPPR [SEQ ID NO: 9] |
| 70 | 87 | 2229.1 | 2230.6 | WFKNGNELNRKNKPENIK [SEQ ID NO: 10] |
| 16 | 38 | 2342.2 | 2343.1 | KDRGSRGKPGPAEGDPSPALPPR [SEQ ID NO: 11] |

The invention claimed is:

1. A method for detecting Alzheimer's Disease, comprising a) determining the concentration of a neuregulin-β isoform having an apparent molecular mass of about 32 kD as determined using SDS-PAGE in a sample to be investigated by using antibodies against said neuregulin-β isoform; and b) comparing the concentration of said neuregulin-β isoform in said sample to a control concentration determined in a sample from a normal individual, wherein a reduced concentration as compared to said control concentration indicates the presence of Alzheimer's Disease and wherein the sample is a nerve cell from the hippocampus.

2. The method according to claim 1, wherein said neuregulin-β isoform has an isoelectric point (pI) in the range from about pH 4.3 to 5.0, and comprises the amino acid sequence of SEQ ID NO:4.

3. The method according to claim 1, wherein the neuregulin-β has an acid isoelectric point.

4. A method for detecting Alzheimer's Disease, comprising
obtaining a sample from a subject wherein the sample is a nerve cell from the hippocampus,
obtaining antibodies specific for a neuregulin-β isoform, and
determining the concentration of said neuregulin-β isoform in said sample by using said antibodies against said neuregulin-β isoform,
wherein a reduced concentration as compared to a control concentration determined in a sample from a normal individual indicates the presence of Alzheimer's Disease, wherein the sample is a nerve cell from the hippocampus, and,
wherein said neuregulin-β isoform has an isoelectric point (pI) in the range from about pH 4.3 to 5.0, has an apparent molecular mass of about 32 kD as determined using SDS-PAGE and comprises the amino acid sequence of SEQ ID NO:4.

* * * * *